United States Patent
Faizer

(10) Patent No.: US 10,398,579 B2
(45) Date of Patent: Sep. 3, 2019

(54) CATHETER SYSTEM WITH GUIDEWIRE COMPARTMENTALIZATION

(71) Applicant: Regents of the University of Minnesota, Minneapolis, MN (US)

(72) Inventor: Rumi Faizer, Little Canada, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 131 days.

(21) Appl. No.: 15/412,501

(22) Filed: Jan. 23, 2017

(65) Prior Publication Data

US 2017/0209291 A1 Jul. 27, 2017

Related U.S. Application Data

(60) Provisional application No. 62/286,033, filed on Jan. 22, 2016.

(51) Int. Cl.
*A61F 2/954* (2013.01)
*A61M 25/09* (2006.01)

(52) U.S. Cl.
CPC ............. *A61F 2/954* (2013.01); *A61M 25/09* (2013.01)

(58) Field of Classification Search
CPC .. A61F 2/954; A61F 2/95; A61F 2/958; A61F 2/962; A61F 2/966; A61F 2/97; A61F 2/2427; A61F 2/243; A61F 2/2433; A61F 2/2436; A61F 2/2439; A61F 2002/9505; A61F 2002/9511; A61F 2002/9517; A61F 2002/9522; A61F 2002/9528; A61F 2002/9534; A61F 2002/9583; A61F 2002/9586; A61F 2002/9665; A61M 25/09; A61M 25/0026; A61M 25/0028; A61M 25/0029; A61M 25/003; A61M 25/0032; A61M 25/09016; A61M 25/09025; A61M 25/09033; A61M 25/09041;

(Continued)

(56) References Cited

U.S. PATENT DOCUMENTS 5,389,082 A 2/1995 Baugues et al.
5,591,228 A 1/1997 Edoga
(Continued)

*Primary Examiner* — Shaun L David
*Assistant Examiner* — Brigid K Byrd
(74) *Attorney, Agent, or Firm* — Dicke, Billig & Czaja, PLLC

(57) ABSTRACT

A catheter system including a delivery sheath and a wire management device. The wire management device is slidably disposed within a lumen of the sheath, and includes a shaft and at least two vane assemblies. The vane assemblies each project from an exterior surface of the shaft and are circumferentially spaced from one another. Further, the vane assemblies are collapsible to a collapsed stated when disposed within the lumen, and are configured to self-expand from the collapsed state toward a normal, expanded state when released from the lumen. The catheter assembly generates a plurality of compartments that are separated from one another by the vane assemblies and along which individual guidewires can be tracked. The compartments maintain the guidewires separate from one to prevent possible twisting. An advancing endograft delivery device tracked over the guidewires collapses the vane assemblies, coalescing the compartments into a single compartment during endograft deployment.

20 Claims, 12 Drawing Sheets

(58) Field of Classification Search
CPC .......... A61M 25/0169; A61M 25/0172; A61M 2025/0031; A61M 2025/0034; A61M 2025/0035; A61M 2025/0036; A61M 2025/0037; A61M 2025/0039; A61M 2025/004; A61M 2025/09116; A61M 2025/09125; A61M 2025/0177; A61M 2025/1056; A61B 2017/22049; A61B 2017/0046; A61B 2017/00464; A61B 2017/00469; A61B 2017/00473
USPC ........................................................ 606/108
See application file for complete search history.

(56) References Cited

U.S. PATENT DOCUMENTS

| | | | |
|---|---|---|---|
| 6,855,159 | B1 | 2/2005 | Tanner et al. |
| 8,728,011 | B2 | 5/2014 | Khoury |
| 2006/0069323 | A1 | 3/2006 | Elkins et al. |
| 2007/0250001 | A1 | 10/2007 | Hilaire et al. |
| 2009/0259285 | A1 | 10/2009 | Duane et al. |
| 2009/0326634 | A1 | 12/2009 | Vardi |
| 2010/0069838 | A1* | 3/2010 | Weber ................ A61M 31/002 604/103.02 |
| 2011/0022026 | A1* | 1/2011 | Sorensen ............. A61K 9/0024 604/507 |
| 2011/0137155 | A1* | 6/2011 | Weber ................ A61B 5/02007 600/424 |
| 2012/0022636 | A1 | 1/2012 | Chobotov |

* cited by examiner

CATHETER SYSTEM WITH GUIDEWIRE COMPARTMENTALIZATION

CROSS-REFERENCE TO RELATED APPLICATIONS

This Non-Provisional patent application claims the benefit of the filing date of U.S. Provisional Patent Application Ser. No. 62/286,033, filed Jan. 22, 2016, entitled "CATHETER SYSTEM WITH GUIDEWIRE COMPARTMENTALIZATION," the entire teachings of which are incorporated herein by reference.

BACKGROUND

The present disclosure relates to catheter and guidewire systems. More particularly, it relates to catheter-based systems employing two or more guidewires to deliver to a therapeutic device to a patient.

A variety of different therapies can be delivered within the human body by catheter systems or devices. Therapeutic devices such as stents, stent grafts, endografts, filters, dilation balloons are but a few examples, and are conventionally delivered to a target site in a contracted or compressed state within a catheter. The device is typically loaded at a distal end of the catheter; once properly located, the catheter is proximally retracted and/or the device is distally advanced.

To aid in positioning of the distal end of the catheter within the body, typically a guidewire is first navigated to the treatment area. After the guidewire has been positioned, the catheter can be directed along or over the guidewire, bringing the distal end of the catheter to a desired position. In this regard, the catheter will form at least one lumen that slidably receives the guidewire. For many procedures, the catheter will provide two (or more lumens), with at least one of the lumens dedicated to the guidewire.

In addition to facilitating catheter placement, guidewires are also employed to achieve desired arrangement or deployment of the catheter-delivered device in some instances. For example, devices intended to branch across bodily vessel bifurcation (e.g., a bifurcated stent graft). In vessel bifurcations, a main vessel splits into two branch vessels. Implanting stents or stent grafts in bifurcations is particularly problematic because of the need to precisely locate the stent both longitudinally and radially in the bifurcation, for example to locate a side opening or branch of the stent graft to face and extend into the branching vessel. Such devices and corresponding methods of delivery require complicated manipulations and precise delivery to specific target locations. Where the stent graft or other device to be implanted provides multiple side openings (fenestrations) or branches each intended to face or be located within a separate branch vessel (e.g., an abdominal aortic aneurysm stent graft), the procedure is even more complicated. Oftentimes, multiple guidewires are required to properly align each opening with respect to a corresponding branch vessel.

Where a particular procedure benefits from the provision of multiple guidewires to effectuate alignment of the device to be implanted relative to the native anatomy, clinicians prefer that the multiple guidewires be delivered through a single catheter (as opposed to providing a separate catheter and access approach for each guidewire). While loading of the guidewires to the catheter or delivery sheath and subsequent delivery of the device over the guidewires once in place is in theory straightforward, problems may arise. In particular, due the tortuous delivery path presented by many procedures and/or the manipulations of the guidewires in order to achieve necessary vessel or side branch location, two or more of the guidewires oftentimes wrap or twist about one another. Wrapping of the guidewires can be highly problematic as the device cannot then be readily advanced over the guidewires.

SUMMARY

The inventor of the present disclosure recognizes that a need exists for a catheter system that overcomes one or more of the above-mentioned problems.

Some aspects of the present disclosure are directed toward a catheter system including a delivery sheath and a wire management device. The delivery sheath defines a lumen and a distal end. The wire management device is slidably disposed within the lumen, and includes an inner shaft, a first vane assembly and a second vane assembly. The inner shaft defines a centerline. Each of the vane assemblies projects from an exterior surface of the inner shaft and defines an outer edge opposite the inner shaft. The first and second vane assemblies are circumferentially spaced from one another relative to a circumference of the inner shaft. Further, the first and second vane assemblies are collapsible to a collapsed stated when disposed within the lumen, the collapsed state including the vane assembly bearing against an interior surface of the delivery sheath. Additionally, the vane assemblies are configured to self-expand (relative to the inner shaft) from the collapsed state toward a normal, expanded state when released from the lumen. In this regard, a radial distance between the corresponding outer edge and the centerline in the expanded state is greater than the radial distance in the collapsed state. With this construction, the catheter assembly generates a plurality of compartments that are separated from one another by the vane assemblies. At a region where the vane assemblies are disposed within the delivery sheath, the compartments are radially closed by the delivery sheath; conversely, at a region where the vane assemblies are free of the delivery sheath, the compartments are radially open. During use, individual guidewires can be tracked through individual compartments, with the compartments maintaining the guidewires separate from one another and minimizing or preventing possible twisting of two (or more) of the guidewires. Further, when located within a bodily vessel and released from the delivery sheath, the vane assemblies self-expand into contact with a wall of the bodily vessel, effectively "closing" the otherwise radially open compartment. A guidewire can be further tracked along the so-formed compartment and manipulated to locate or cannulate a side branch ostium along the bodily vessel wall.

In some embodiments, the wire management device includes three or more of the vane assemblies. In other embodiments, each of the vane assemblies includes a plurality of aligned, thin bristles that readily collapse in a desired fashion or direction, and self-revert toward an expanded state. In general terms, the vane assemblies of the present disclosure are configured to define portions of guidewire-receiving compartments as mentioned above. To successfully keep these compartments separated, the vane assemblies should reach out from the inner shaft (or other central hub) to the perimeter of a vessel wall within which the wire management device is located in a radial fashion. Contact should be made with the vessel wall along the entire path so that guidewires do not have a "gap" through which they could cross into an adjacent compartment. For this to work in vessels with changing caliber or angles, the vane assemblies may be able to adjust in their radial reach and have a natural propensity to push outward. The vane assemblies may also act as a barrier to the guidewire or the delivery sheath; they may not have functional openings. A second optional property of the vane assemblies is that they should be easily collapsible when they encounter a force driving up the lumen. This will allow for a device that is tracked on two (or more) wires carried by the wire management device that are otherwise in adjacent compartments to be advanced in the intended direction. Thus, for example, when used as part of an endograft delivery procedure, the vane assemblies will collapse from the expanded state by an advancing endograft delivery device that is tracked simultaneously on the guidewires within the separate compartments to effectively coalesce the compartments into a single compartment during endograft deployment. The wire management device is retracted out of the patient once the endograft is in its final position and prior to final deployment (e.g., unsheathing and expansion) of the endograft.

DETAILED DESCRIPTION

Figure 1:
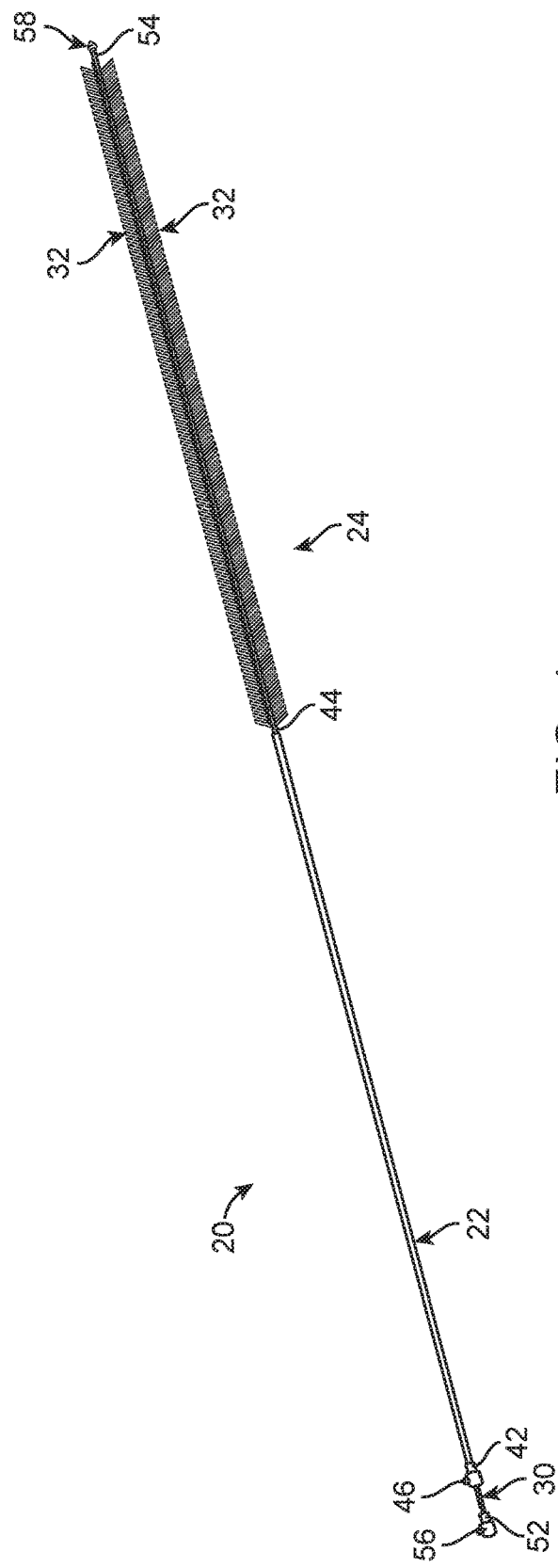
FIG. 1 is a perspective view of a catheter system in accordance with principles of the present disclosure.

One embodiment of a catheter system 20 in accordance with principles of the present disclosure is shown in FIG. 1. The catheter system 20 includes a delivery sheath 22 and a wire management device 24. Details on the various components are provided below. In general terms, the wire management device 24 includes an inner shaft 30 and a plurality of vane assemblies 32 (two of which are visible in FIG. 1), and is configured to be slidably received within a lumen of the delivery sheath 22. In particular, the vanes 32 are collapsible from a normal, expanded state (reflected by FIG. 1) outside of the delivery sheath 22 to a collapsed state within the delivery sheath 22. Further, the wire management device 24 defines a plurality of compartments, each configured to slidably receive a guidewire (not shown) as described below and that can be considered components of the catheter systems of the present disclosure in some embodiments.

The delivery sheath 22 can assume a wide variety of forms appropriate for accessing and traversing a bodily lumen (or lumens) of a human patient. Thus, the delivery sheath 22 can be akin to a conventional catheter (e.g., a biologically compatible tube with sufficient column strength for traversing tortuous anatomy that may optionally incorporate steering features), having a tubular construction defining a lumen (hidden in FIG. 1, but referenced generally at 40 in FIG. 2). The delivery sheath 22 defines opposing, proximal and distal ends 42, 44. The lumen is open to the distal end 44, and in some embodiments is also open to the proximal end 42. An optional delivery sheath hub 46 can be attached to or carried by the proximal end 42.

The wire management device 24 provides the inner shaft 30 as an elongated, tubular body defining at least one internal passageway or lumen 50 (hidden in FIG. 1, but shown, for example, in FIG. 7A) in some embodiments. In other embodiments, the inner shaft 30 can be a solid body. Regardless, the inner shaft 30 is flexible yet exhibits sufficient columnar strength for traversing tortuous anatomy, and defines opposing, proximal and distal ends 52, 54. As made clear below, a diameter of the inner shaft 30 is less than a diameter of the lumen (not shown) formed by the delivery sheath 22. An inner shaft hub 56 is optionally attached to or carried by the proximal end 52. A guide cone 58 can be formed by or attached to the distal end 54 in some embodiments. Where provided, the guide cone 58 can assume a variety of configurations promoting atraumatic contact with bodily tissue, and can define a central passage that is open to the optional internal passageway 50 of the inner shaft 30.

Figure 2:
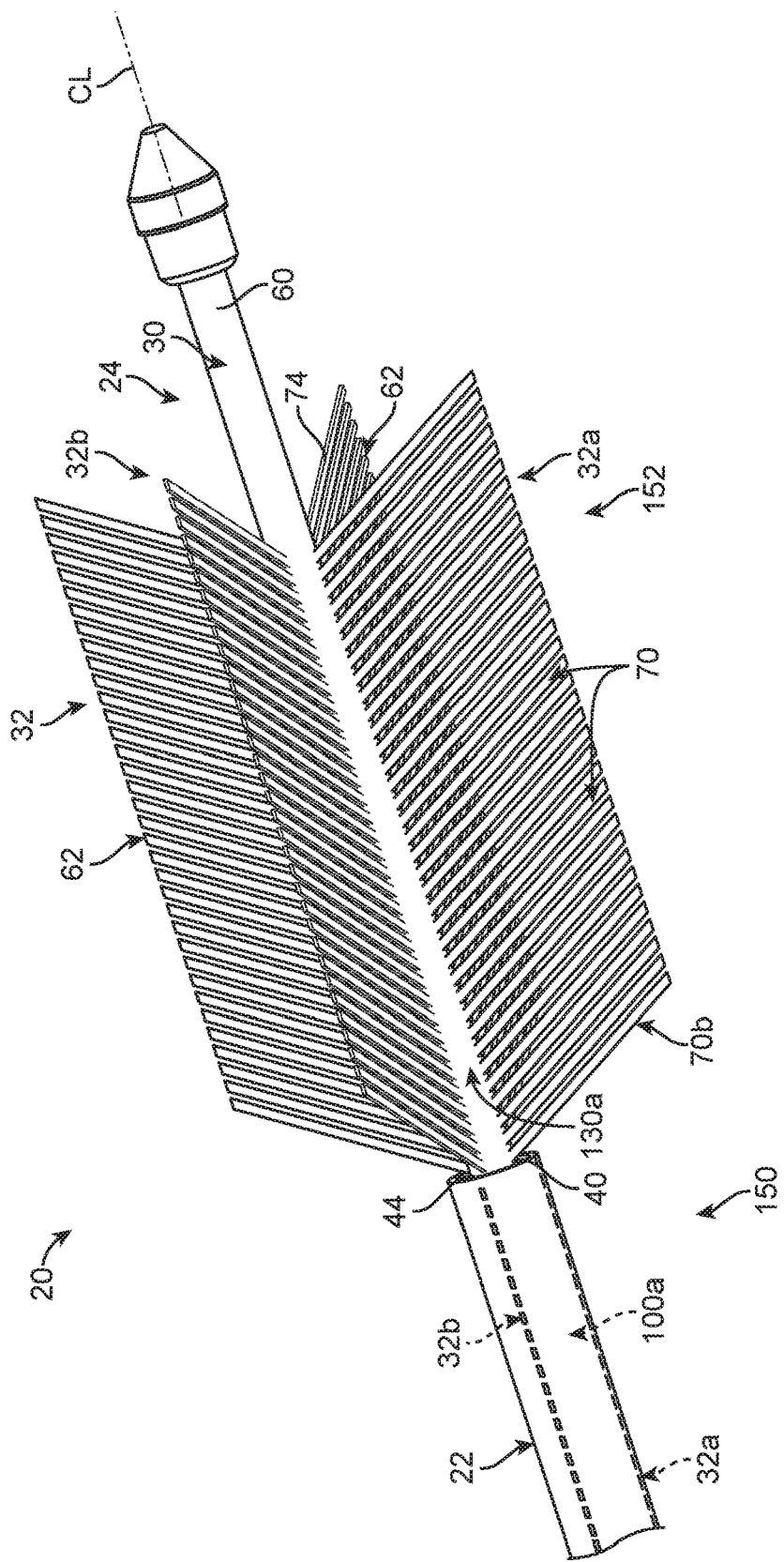
FIG. 2 is an enlarged perspective view of a portion of the system of FIG. 1.

The vane assemblies 32 can assume a wide variety of forms conducive to providing the expanded and contracted states as described below. For example, FIG. 2 illustrates a portion of each of the vane assemblies 32 in greater detail. As a point of reference, in the view of FIG. 2, the delivery sheath 22 has been distally advanced relative to the wire management device 24 and/or the wire management device 24 has been proximally retracted relative to the delivery sheath 22 as compared to the arrangement of FIG. 1. In the arrangement of FIG. 2, then, a first portion of each the vane assemblies 32 is in a collapsed state (located within the lumen 40 (referenced generally) of the delivery sheath 22), and a second portion is exposed distally beyond the distal end 44 of the delivery sheath 22 and self-assumes the normal, expanded state. Further, while FIG. 2 illustrates the wire management device 24 as including four of the vane assemblies 32, any other number, either greater or lesser, is equally acceptable (e.g., in other embodiments, six of the vane assemblies 32 are provided). The wire management devices of the present disclosure include at least two of the vane assemblies 32.

The vane assemblies 32 each project in a radial fashion (relative to a centerline CL of the inner shaft 30) from an exterior surface 60 of the inner shaft 30, and are circumferentially spaced from one another about a circumference of the inner shaft 30. Further, each of the vane assemblies 32 terminates at an outer edge 62 opposite the inner shaft 30. The vane assemblies 32 can have an identical construction in some embodiments. For example, and as identified for the first vane assembly 32a in FIG. 2, the vane assemblies 32 can each include or consist of a plurality of bristles 70. The bristles 70 can be longitudinally aligned with one another (e.g., aligned parallel to the centerline CL of the inner shaft 30), and collectively define the corresponding outer edge 62. While, for ease of understanding, FIG. 2 illustrates a discernable spacing between immediately adjacent ones of the bristles 70 of the first vane assembly 32a, in other embodiments the bristles 70 are more closely positioned relative to each other, collectively forming a membrane-like or barrier-like structure (e.g., the bristles 70 are confluent and effectively create a membrane due to close apposition of the bristles 70 so as to, for example, prevent a guidewire from passing "through" the vane assembly 32). In other embodiments, the vane assemblies 32 can each have a more homogenous or integral structure.

The vane assemblies 32 are each formed of a biocompatible material (e.g., PTFE or similar material). A material and construction of the vane assemblies 32 is selected so as to render the corresponding outer edge 62 relatively soft or compliant, appropriate for atraumatic contact with bodily tissue. The outer edge 62, or an entirety of the vane assembly 32, can be coated with a hydrophilic or similar material that is non-thrombogenic (e.g., resistance to thrombosis in the vascular system).

Further, the vane assemblies 32 are each configured to readily deflect from the expanded state to the collapsed state when directed into the lumen 40 of the delivery sheath 22, and self-revert or self-expand toward the expanded state when released from the confines of the delivery sheath 22. Further, the vane assemblies 32 are each configured to collapse from the expanded state against the pressure of a separate delivery device (not shown), for example an endograft delivery system, being advanced over guidewires (not shown) carried by the wire management device 24 as described in greater detail below.

Figure 3:
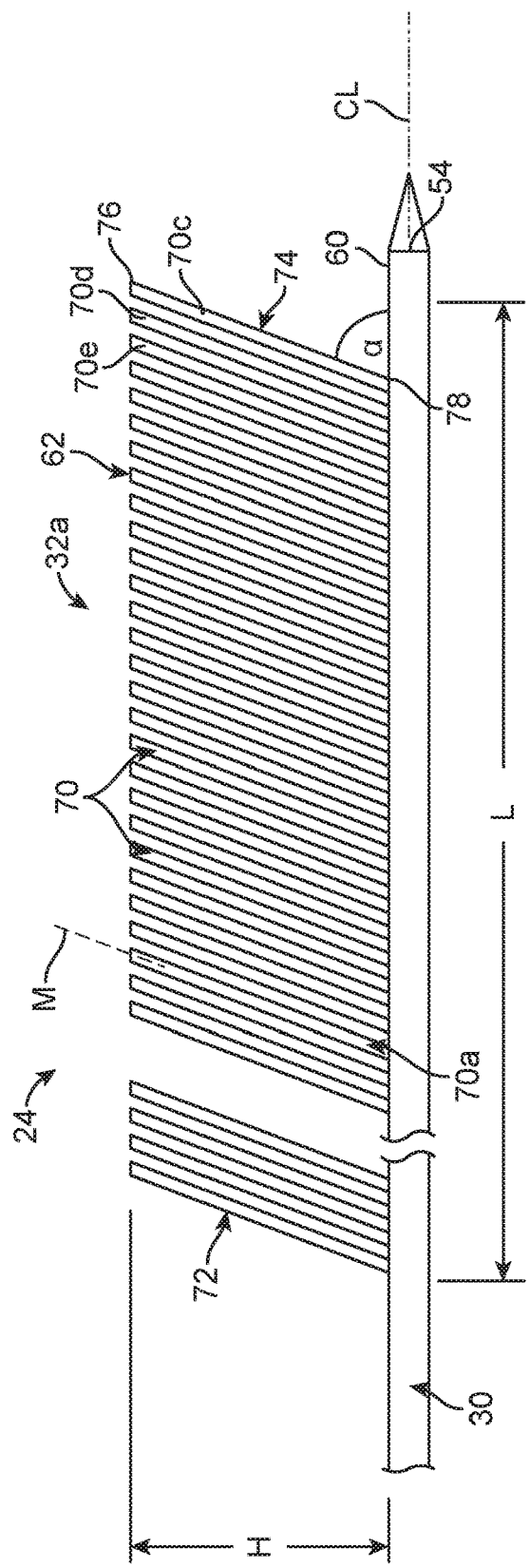
FIG. 3 is a simplified side view of a portion of a wire management device useful with the system of FIG. 1 and with portions removed.

In some optional embodiments, the vane assemblies 32 are each configured to more readily deflect to the collapsed state with distal advancement of the delivery sheath 22 and/or proximal retraction of the wire management device 24, such as by incorporating a shape bias in the distal direction. For example, FIG. 3 illustrates the inner shaft 30 and the first vane assembly 32a in isolation. The plurality of bristles 70 collectively defines the vane assembly 32a to have a proximal edge 72 opposite a distal edge 74. The distal edge 74 projects from the exterior surface 60 of the inner shaft 30 to the outer edge 62, with this projection defining a bias angle α. In the expanded state of FIG. 3, the bias angle α can be an acute angle, for example in the range of 25°-85°, and faces or is open to the distal end 54. That is to say, the distal edge 74 can be viewed as defining a leading point 76 at the outer surface 62 and a trialing point 78 at the exterior surface 60 of the inner shaft 30; the distal bias of the vane assembly 32a in the expanded state can include the leading point 76 being distal the trailing point 78, or the leading point 76 being longitudinally closer to the distal end 54 as compared to the trailing point 78 (the longitudinal direction being relative to the centerline CL of the inner shaft 30). A similar relationship can be established at the proximal edge 72. Each of the bristles 70 can exhibit this same geometry. For example, each of the bristles 70 can have a shape akin to a parallelogram, and are arranged on the exterior surface 60 so as to be skewed in the distal direction. A major axis M (identified for a first bristle 70a in FIG. 3) forms the same bias angle α relative to the exterior surface 60 as described above. With additional reference to FIG. 2, then, as the delivery sheath 22 is distally advanced relative to the wire management device 24 (and/or as the wire management device 24 is proximally retracted relative to the delivery sheath 22) and the distal end 44 of the delivery sheath 22 comes into contact with an immediately next one of the expanded state bristles 70 (e.g., the bristle 70b identified in FIG. 2 for the first vane assembly 32a), the so-contacted bristle 70 readily collapse toward the inner shaft 30 due to the distal bias. Conversely, as the delivery sheath 22 is proximally retracted relative to the wire management device 24 (and/or as the wire management device 24 is distally advanced relative to the delivery sheath 22) and an immediately next of the collapsed state bristles 70 is brought distally beyond the distal end 44 of the delivery sheath 22, the so-released bristle 70 self-expands back toward the normal, expanded state. In other embodiments, the bias angle α can be obtuse or can be 90°. The vane assemblies 32 can have other constructions that provide these same features that may or may not include a plurality of bristles or similarly-shaped bodies.

Figure 4A:
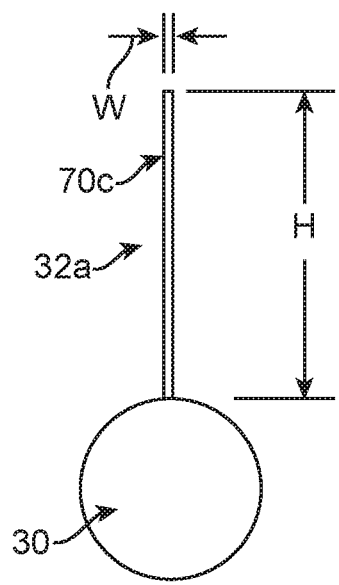
FIG. 4A is a simplified end view of the wire management device of FIG. 3.
Figure 4B:
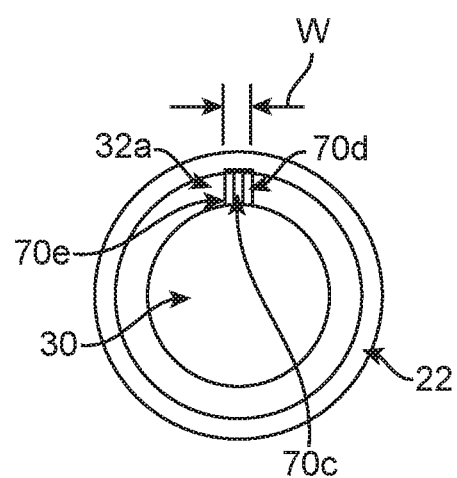
FIG. 4B is a simplified end view of system of FIG. 1, including the wire management device of FIG. 4A disposed within a delivery sheath.

In addition to being readily deflected or collapsed, the vane assemblies 32 are each configured to distally collapse in a relatively uniform fashion, whereby an effective width of the vane assembly 32 does not overtly expand. By way of reference, FIG. 3 reflects the plurality of bristles 70 as collectively forming the first vane assembly 32a to have a length L and a height H. With additional reference to FIG. 4A the first vane assembly 32a also has a width W (exaggerated in the view of FIG. 4A for ease of understanding). The vane assemblies 32 have an elongated shape such that the length L is greater than the height H and the width W. Further, while the height H will decrease in transitioning from the expanded state to the collapsed state, in at least the expanded state, the height H is greater than the width W. With these definitions in mind, in the expanded state of FIG. 4A, the bristles 70 are longitudinally aligned such that in the end view of FIG. 4A, only a distal-most bristle 70c is visible and the width W of the first vane assembly 32a is commensurate with the width of each individual bristle 70. As the first vane assembly 32a is caused to collapse due to manipulation of the wire management device 24 relative to the delivery sheath 22, the individually collapsing bristles 70 slide along a side of immediately distal bristles 70. Thus, and as generally reflected by the end view of FIG. 4B in which the first vane assembly 32a has been caused to collapsed by an interface with the delivery sheath 22, bristles 70d, 70e have collapsed along opposite sides of the distal-most bristle 70c. Thus, while there may be some side-to-side overlap between adjacent ones of the bristles 70 in the collapsed state, the width W of the first vane assembly 32a is not overtly increased, and is effectively defined by the collective widths of no more than a few individual bristles 70.

Returning to FIG. 2, with embodiments in which the vane assemblies 32 are formed by the plurality of bristles 70 as described above, the vane assemblies 32 are feather-like or akin to a feather. If one runs one's finger up the shaft of a feather, the vanes of the feather will collapse and flatten with little force. The vanes of the feather, however, provide sufficient surface tension to function as a fan; the barbs carried by each vane tend to stick together to create a membrane that prevents even air from escaping across it.

Figure 5:
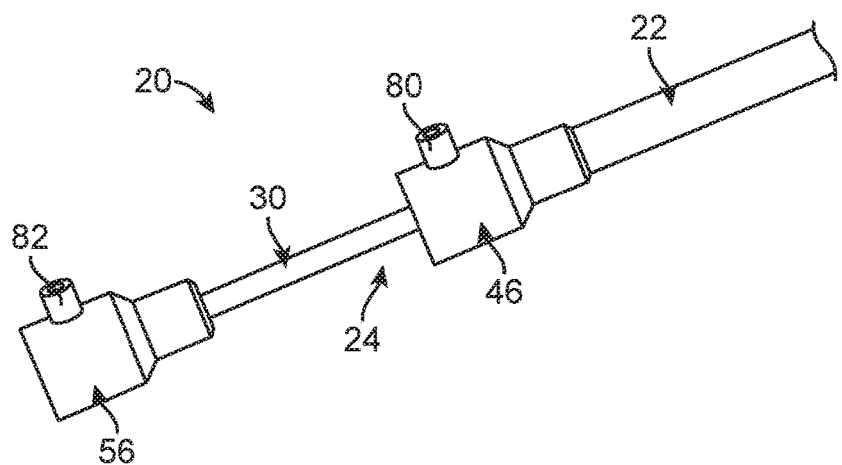
FIG. 5 is an enlarged perspective view of a proximal portion of the system of FIG. 1.

With the above descriptions in mind, and returning to FIG. 1, upon final assembly, the catheter system 20 can be readily transitioned to and from the illustrated fully deployed arrangement (in which the vane assemblies 32 are distally beyond the distal end 44 of the delivery sheath 22) via sliding movement of the delivery sheath 22 relative to the wire management device 24 and/or vice-versa. As a point of reference, FIG. 5 illustrates a proximal region of the catheter system 20 in the deployed arrangement. The inner shaft 30 is slidably disposed within the delivery sheath 22 via the delivery sheath hub 46. The delivery sheath hub 46 can provide a flush port 80 (that in turn can include or carry a fitting connect (e.g., Leuer fitting)) for removal of air from the delivery sheath lumen 40 (FIG. 2) prior to use. The inner shaft hub 56 can similarly provide a flush port 82 for removing air from the internal passageway 50 (FIG. 7A) of the inner shaft 30.

Figure 6:
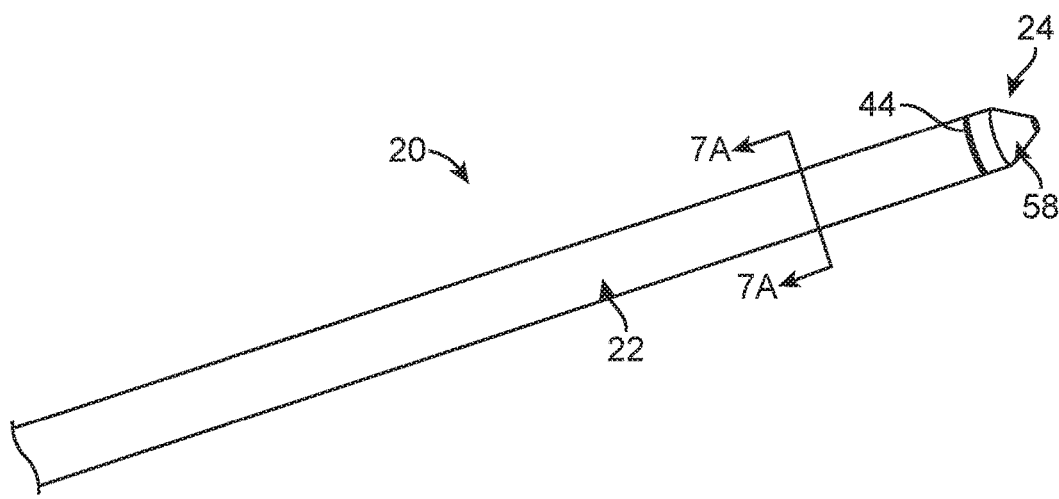
FIG. 6 is an enlarged perspective view of a distal portion of the system of FIG. 1 and in a delivery condition.
Figure 7A:
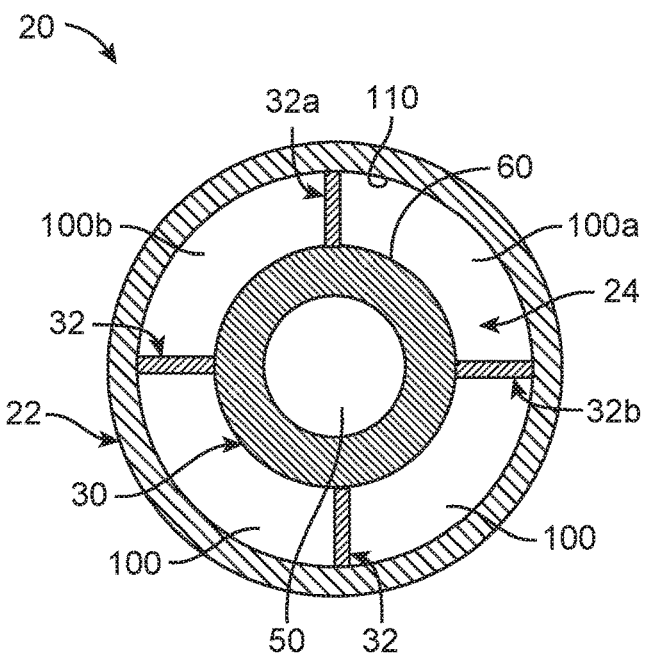
FIG. 7A is a cross-sectional view of a portion of the system of FIG. 6 taken along the line 7A-7A.

In a delivery condition of the catheter system 20 reflected by FIG. 6, the delivery sheath 22 and the wire management device 24 (referenced generally in FIG. 6) are manipulated relative to one another such that the distal end 44 of the delivery sheath 22 abuts the guide cone 58, locating the vane assemblies 32 (hidden in FIG. 6) within the delivery sheath 22 and forced to the collapsed state. FIG. 7A shows that in the delivery condition, the delivery sheath 22 and the wire management device 24 combine to define a plurality of closed compartments 100. In particular, each of the vane assemblies 32 bear against an interior surface 110 of the delivery sheath 22, with circumferentially adjacent ones of the vane assemblies 32 defining opposing sides of a corresponding one of the closed compartments 100. For example, a first closed compartment 100a is labeled in FIG. 7A and is defined by the first and second vane assemblies 32a, 32b, the interior surface 110 of the delivery sheath 22, and the exterior surface 60 of the inner shaft 30. The closed compartments 100 are separated from one another by the corresponding vane assemblies 32 (e.g., a second closed compartment 100b is also identified in FIG. 7A as is separated from the first closed compartment 100a by the first vane assembly 32a), and are open to the distal end 44 (FIG. 6) of the delivery sheath 22. In some embodiments, the closed compartments 100 are also open to the proximal end 42 (FIG. 1) of the delivery sheath 22, although proximal access to one or more of the closed compartments 100 can be provided elsewhere along a length of the delivery sheath 22. FIG. 7A further illustrates the internal passageway or lumen 50 of the inner shaft 30.

Figure 7B:
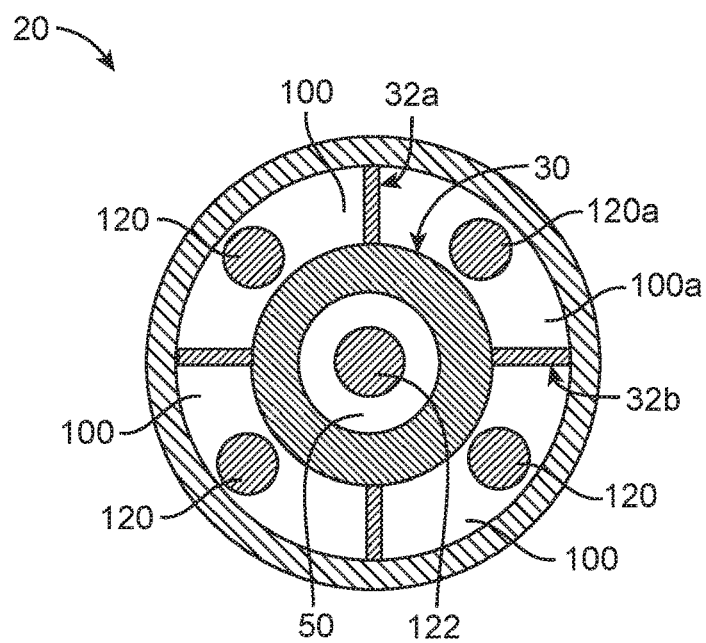
FIG. 7B is the cross-section view of FIG. 7A and further illustrating guidewires useful with the systems of the present disclosure.

The closed compartments 100 are sized and shaped to slidably receive at least one guidewire. For example, FIG. 7B shows the catheter system 20 as further including a plurality of guidewires 120, with each guidewire 120 slidably disposed within a respective one of the closed compartments 100. A main guidewire 122 can also be provided, and is slidably received within the internal passageway 50 of the inner shaft 30.

Figure 8A:
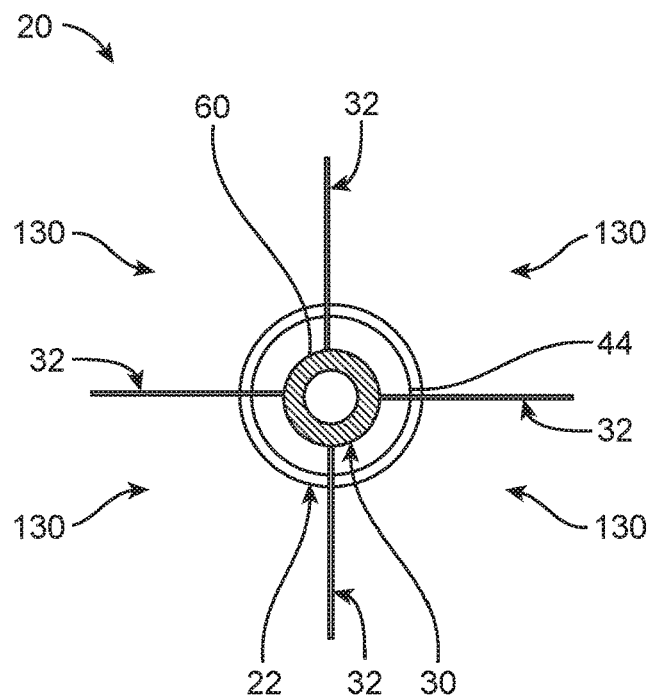
FIG. 8A is a cross-sectional view of a portion of the system of FIG. 2 taken along a deployment region thereof.

When a portion (or entirety) of the vane assemblies 32 are removed from the confines of the delivery sheath 22, that portion of each of the vane assemblies 32 self-reverts toward the expanded state as described above. The exposed portions of the vane assemblies 32 and the exterior surface 60 of the inner shaft 30 combine to form a plurality of open compartments 130 as shown in FIG. 8A. The open compartments 130 represent a continuation of a corresponding one of the closed compartments 100. For example, FIG. 2 generally identifies a first closed compartment 100a and a first open compartment 130a. The first closed compartment 100a is defined between the first and second vane assemblies 32a, 32b, and is continuous to the distal end 44 of the delivery sheath 22. The first open compartment 130a is also defined between the first and second vane assemblies 32a, 32b but is distal the distal end 44 of the delivery sheath 22 and is effectively a continuation of the first closed compartment 100a. Given these explanations, it will be understood that the open compartments 130 exist or are "created" under circumstances where the distal end 44 of the delivery sheath 22 is proximal the distal edge 74 of the vane assemblies 32. Further, the closed compartments 100 exist under circumstances where the distal end 44 of the delivery sheath 22 is distal the proximal edge 72 (FIG. 3) of the vane assemblies 32. When the distal end 44 of the delivery sheath 22 is longitudinally between the proximal and distal edges 72, 74 of the vane assemblies 30 (e.g., the arrangement of FIG. 2), both the closed and open compartments 100, 130 are defined. For ease of understanding, a region of the catheter assembly 20 proximal the distal end 44 of the delivery sheath 22 can be considered a delivery region 150, and a region of the catheter assembly distal the distal end 44 can be considered a deployment region 152. The vane assemblies 32 are in the collapsed state along the delivery region 150 and are in the expanded state along the deployment region 152.

Figure 8B:
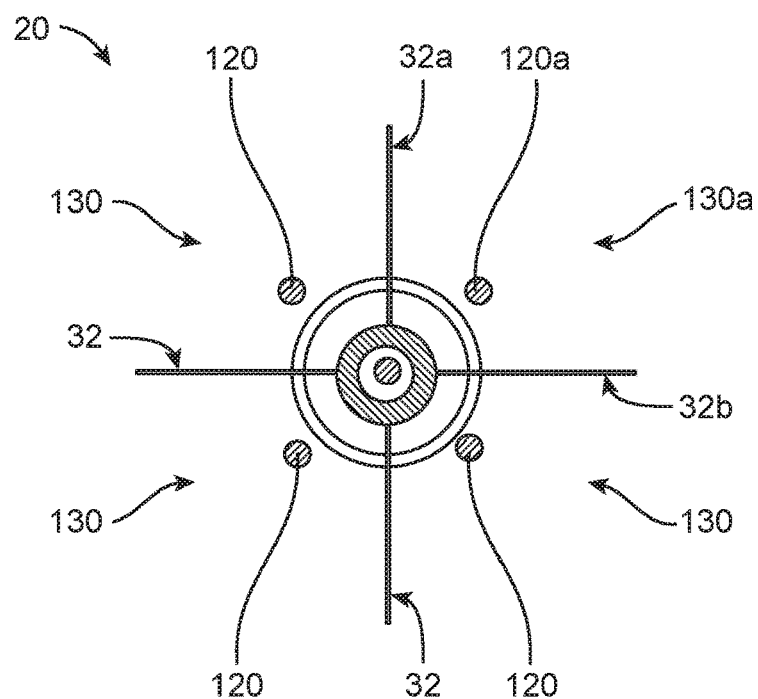
FIG. 8B is the cross-sectional view of FIG. 8A and further illustrating guidewires useful with the systems of the present disclosure.

As illustrated by a comparison of FIGS. 7B and 8B, the guidewire 120 of each closed compartment 100 is readily located within, or directed into, the corresponding open compartment 130. As a point of reference, FIG. 7B is a cross-section of the catheter assembly 20 of FIG. 2 loaded with the guidewires 120 and taken along the delivery region 150 (FIG. 2). FIG. 8B is a cross-section of the same catheter assembly 20 loaded with the same guidewires 120 and taken along the deployment region 152 (FIG. 2). FIG. 7B identifies a first guidewire 120a located and extending within the first closed compartment 100a. FIG. 8B reflects that the same first guidewire 120a is further located and extends within the first open compartment 130a.

Figure 8C:
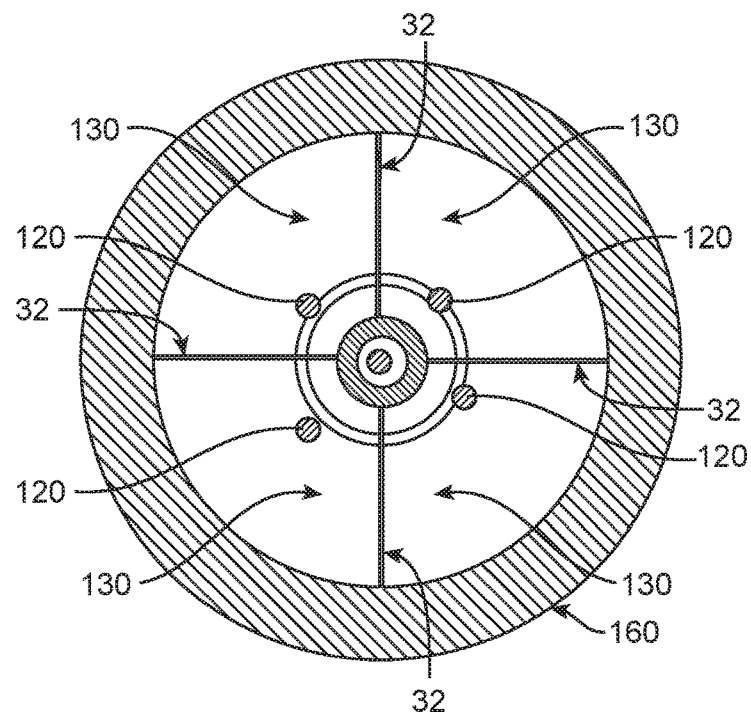
FIGS. 8C and 8D are simplified cross-sectional views illustrating the arrangement of the system of FIG. 8B within a bodily vessel.
Figure 8D:
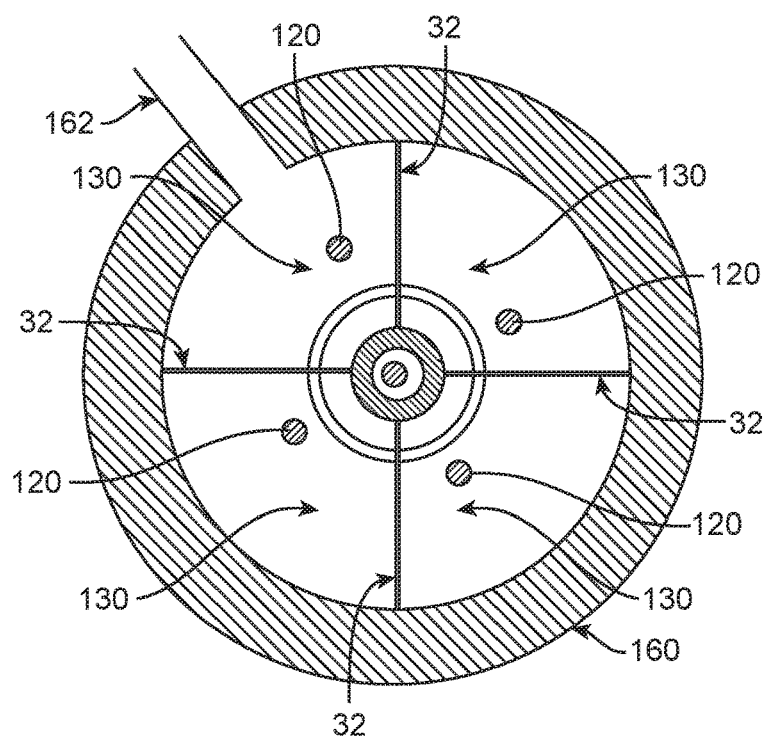

With continued reference to FIGS. 2, 7B, and 8B, each guidewire 120 is constrained or captured in the radial direction (relative to the centerline CL of the inner shaft 30) by the delivery sheath 22 in the corresponding closed compartment 100, and is not radially constrained or captured by the delivery sheath 22 in the corresponding open compartment 130. Thus, the guidewires 120 could each be manipulated radially outside of the corresponding open compartment 130 in the absence of other external structures. As described in greater detail below, during use a bodily vessel can serve as an external structure that closes the open compartments 130, with the catheter systems of the present disclosure being configured in accordance with expected anatomical features of a particular bodily vessel in which the catheter system 20 is deployed. For example, FIG. 8C is a simplified illustration of the catheter system 20 (including the guidewires 120) of FIG. 8B, located within a bodily vessel 160. The wire management device 24 (FIG. 1) is configured in accordance with an expected diameter of the bodily vessel 160, whereby a diameter collectively defined by the vane assemblies 32 in the expanded state is less than the diameter of the bodily vessel 160. Under these circumstance, the exposed portion of the vane assemblies 32 self-expand into contact with the bodily vessel 160; the bodily vessel 160 thus serves to "close" the open compartments 130, preventing overt radial displacement of each of the guidewires 120 away from or outside of the corresponding open compartment 130. However, where an orifice or ostium in the bodily vessel 160 occurs, such as the ostium of a side branch vessel 162 illustrated in FIG. 8D, the guidewire 120 of the open compartment 130 that is otherwise aligned with the ostium can be directed outwardly from the open compartment and through the side branch vessel 162.

Figure 9:
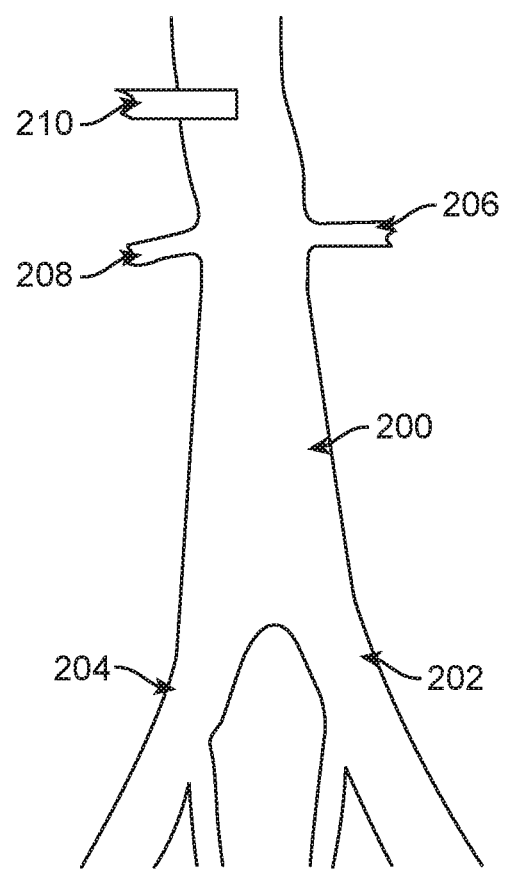
FIG. 9 is a simplified representation of anatomy of an abdominal aorta and related vasculature.

The catheter systems of the present disclosure can be useful for a number of different surgical procedures. In some embodiments, for example, the catheter systems of the present disclosure can be used as part of a coronary stent graft or endograft implantation procedure. As a point of reference, anatomy of an abdominal aorta artery or vessel 200 is shown in simplified form in FIG. 9. Left and right iliac arteries 202, 204 leading to the abdominal aorta 200 are also shown, along with left and right renal arteries 206, 208 and a superior mesenteric artery 210. The renal arteries 206, 208 and the superior mesenteric artery 210 are side branch vessels of the abdominal aorta vessel 200. For certain procedures, such as treatment of an abdominal aortic aneurysm (AAA), it can be beneficial to locate (e.g., cannulate) one or all of the side branch vessels 206-210 (and/or other side branch vessels) with guidewires, such as when implanting a fenestrated or branched AAA stent graft (or similar device). The catheter systems of the present disclosure are useful in these and other procedures.

Figure 10:
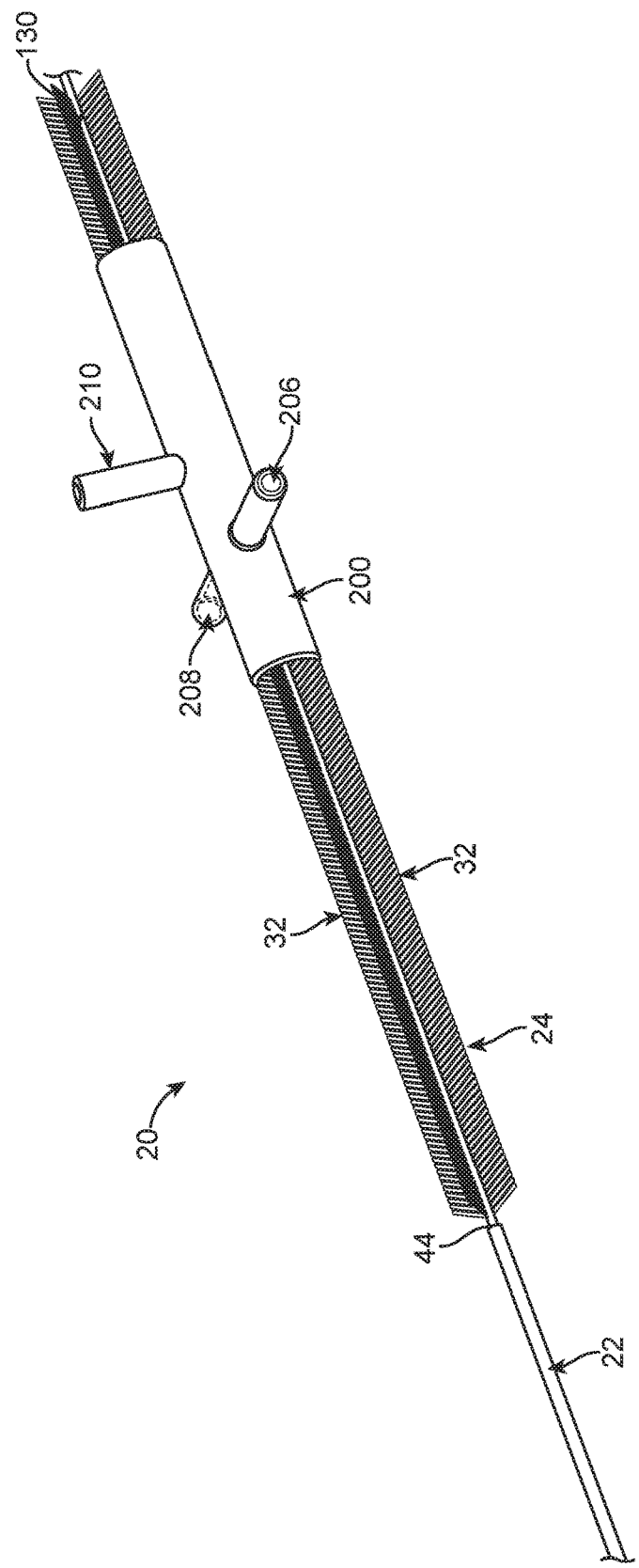
FIG. 10 is a simplified illustration of the catheter system of FIG. 1 arranged at the anatomy of FIG. 9.

In some embodiments, deployment of a stent graft device at the abdominal aorta 200 includes delivering a primary guidewire (e.g., the primary guidewire 122 shown in FIG. 7B) to the abdominal aorta 200 in accordance with conventional techniques (e.g., the primary guidewire is directed or tracked through an incision at a femoral artery, through one of the iliac arteries 202, 204 and into the abdominal aorta 200). The primary guidewire is located at or beyond the bifurcations of the side branch vessels 206-210. As part of, or following, placement of the primary guidewire, and with additional reference to FIG. 1, the delivery sheath 22 is similarly tracked to the abdominal aorta 200. The wire management device 24 is loaded over the primary guidewire (e.g., at the internal passageway 50 (FIG. 7A) of the inner shaft 30) and tracked to the abdominal aorta 200. Guidewires are then loaded into respective ones of the closed compartments 100 (FIG. 7A) via the proximal end 42 of the delivery sheath 22, are tracked to the abdominal aorta 200, and are then manipulated to locate or cannulate the side branch vessels 206-210. For example, FIG. 10 illustrates the catheter system 20 relative to a simplified representation of portions of the abdominal aorta 200, the renal arteries 206, 208, and the superior mesenteric artery 210. The delivery sheath 22 is at least partially retracted relative to the wire management device 24, such that at least a portion of each of the vane assemblies 32 is exposed (relative to the distal end 44 of the delivery sheath 22) and self-assumes the expanded state. The distal end 44 of the delivery sheath 22 is proximal the side branch vessels 206-210, such that the open compartments 130 (one of which is referenced generally in FIG. 10) extend along the abdominal aorta 200 and to a region of the side branch vessels 206-210. Commensurate with the above descriptions, the wire management device 24 is configured in accordance with expected dimensions of the abdominal aorta 200 such that the vane assemblies 32 are each in contact with an inner face of the abdominal aorta 200. The abdominal aorta 200 thus "closes" the open compartments 130. As a result, individual guidewires (not shown) tracked along a respective one of the open compartments 130 are consistently maintained separate from one another, and can be individually manipulated to locate or cannulate a corresponding one of the side branch vessels 206-210 (that is otherwise aligned with a respective one of the open compartments 130).

Figure 11:
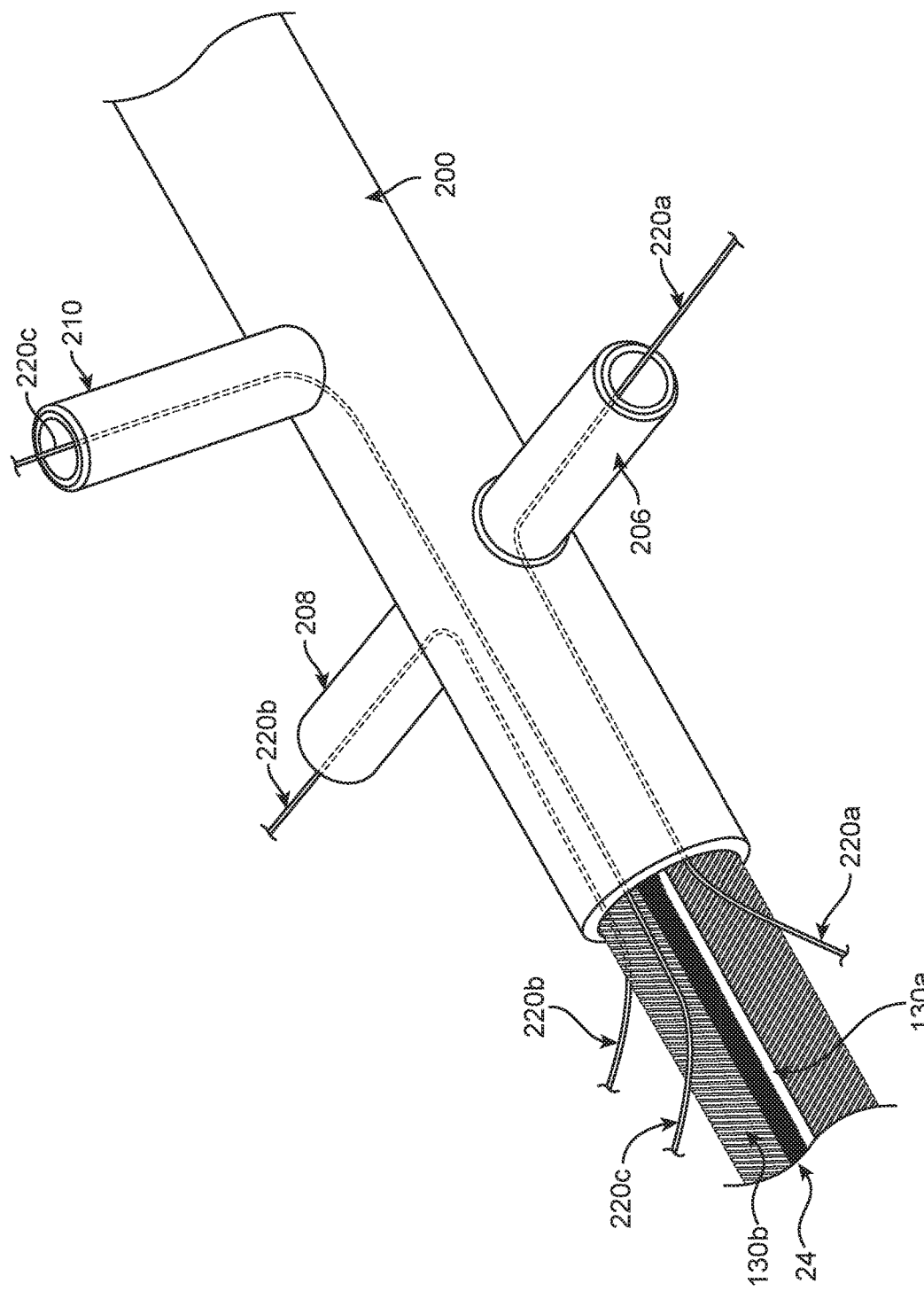
FIG. 11 is an enlarged perspective view of the arrangement of FIG. 10 and further illustrating deployment of guidewires.

For example, FIG. 11 is an enlarged view of a portion of the arrangement of FIG. 10, and further illustrates first-third guidewires 220a-220c. The wire management device 24 is arranged such that a first one of the open compartments 130a (referenced generally) is aligned with, or is open relative to, the left renal artery 206. A second one of the open compartments 130 (hidden in FIG. 11) is aligned with, or open relative to, the right renal artery 208; a third one of the open compartments 130b (referenced generally) is aligned with, or open relative to, the superior mesenteric artery 210. The first guidewire 220a has been tracked to and along the first open compartment 130a, and then manipulated to locate or cannulate the left renal artery 206. The second guidewire 220b has similarly been manipulated to locate or cannulate the right renal artery 208, and the third guidewire 220c has been manipulated to cannulate the superior mesenteric artery 210. A fourth guidewire 220d (not shown in FIG. 11, but illustrated in FIG. 12) can similarly be tracked or located in a fourth one of the open compartments, extending beyond the side branch vessels 206-210. All of the guidewires 220a-220d are maintained separate from one another along the corresponding open compartment 130 (and corresponding closed compartment 100 (not shown)).

Figure 12:
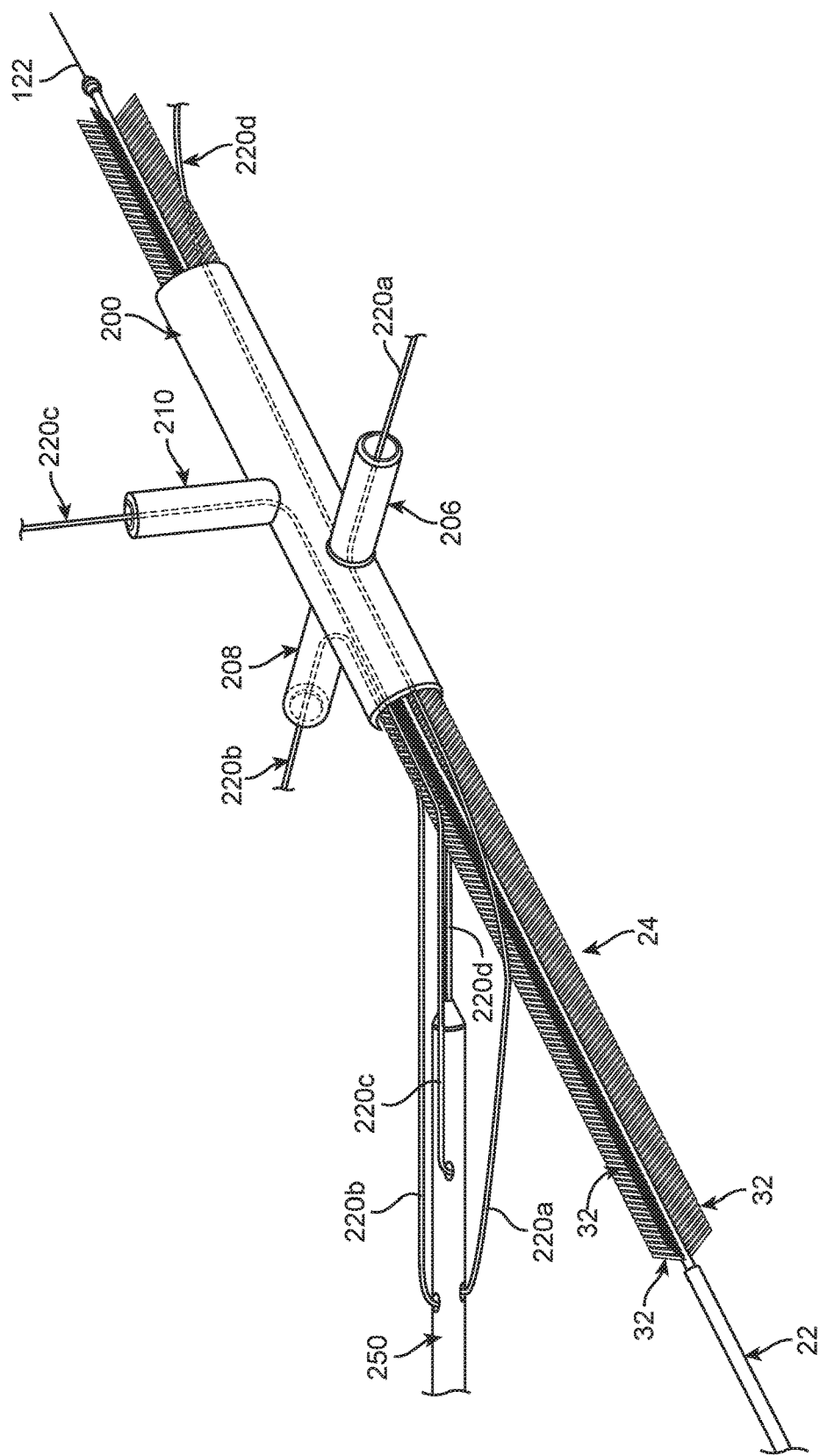
FIG. 12 is a simplified perspective view of the arrangement of FIG. 11 and further illustrating loading of an implantable device via the deployed guidewires.

Once the side branch vessels 206-210 have been cannulated, the stent graft can then be delivered to the target region over the guidewires 220a-220d as generally represented by FIG. 12. In particular, a vascular graft delivery device 250 maintaining a vascular graft (not shown) is loaded over the guidewires 220a-220d. As the vascular graft delivery device 250 is then advanced to the target region, the exposed portion of each of the vane assemblies 32 will readily collapse in accordance with the descriptions above, allowing the vascular graft delivery device 250 to easily track over the guidewires 220a-220d. Prior to collapsing due to the presence of the vascular graft delivery device 250, the vane assemblies 32 continue to separate the guidewires 220a-220d from one another, preventing the guidewires 220a-220d from becoming twisted. However, because the vane assemblies 32 are configured to readily collapse from the expanded state against the pressure of the advancing vascular graft delivery device 250, the vascular graft delivery device 250 can be delivered to the target site as desired, with the compartments 130 (FIG. 11) coalescing into a single compartment during, and only during, deployment of the graft. Once the vascular graft delivery device 250 is located at a desired position relative to the abdominal aorta 200, the wire management device 24 and the primary guidewire 122 can be withdrawn. The vascular graft delivery device 250 is then operated to deploy the vascular graft, with the guidewires 220a-220d serving to confirm or facilitate desired placement of the vascular graft (or components thereof).

The AAA stent graft deployment procedure described above is but one non-limiting example of a procedure utilizing the catheter systems of the present disclosure. A number of other procedures can be performed that make use of more or less than four guidewires. Multiple other procedures benefiting from subdivision of a tube, such as procedures in a patient's airway or GI tract, are also envisioned by the present disclosure.

Although the present disclosure has been described with reference to preferred embodiments, workers skilled in the art will recognize that changes can be made in form and detail without departing from the spirit and scope of the present disclosure.

What is claimed is:
1. A catheter system comprising:
a delivery sheath defining a lumen and a distal end;

a wire management device slidably disposed within the lumen, the wire management device including:
  an inner shaft defining a centerline,
    a first vane assembly projecting from an exterior surface of the inner shaft and defining an outer edge opposite the inner shaft,
    a second vane assembly projecting from the exterior surface and defining an outer edge opposite the inner shaft, the second vane assembly being circumferentially spaced from the first vane assembly relative to a circumference of the inner shaft;
    wherein the first and second vane assemblies are feather-like;
  wherein the first and second vane assemblies are collapsible to a collapsed state when disposed within the lumen, the collapsed state including the respective vane assembly bearing against an interior surface of the delivery sheath;
  and further wherein the first and second vane assemblies are configured to self-expand from the collapsed state toward a normal, expanded state when released from the lumen, a radial distance between the corresponding outer edge and the centerline in the expanded state being greater than the radial distance in the collapsed state.

2. The catheter system of claim 1, wherein the vane assemblies are configured to collapse from the expanded state upon insertion into the lumen.

3. The catheter system of claim 1, wherein the radial distance between the outer edge and the inner shaft relative to the centerline in the expanded state of each of the vane assemblies is greater than a radius of the delivery sheath.

4. The catheter system of claim 1, wherein the catheter system is configured to provide a delivery condition in which at least a portion of each of the first and second vane assemblies is disposed within the lumen, and further wherein the loaded condition includes the wire management device and the delivery sheath combining to define first and second closed compartments.

5. The catheter system of claim 4, wherein the first and second closed compartments are open to the distal end of the delivery sheath.

6. The catheter system of claim 5, wherein the delivery sheath defines a proximal end opposite the distal end, and further wherein the first and second closed compartments are open to the proximal end.

7. The catheter system of claim 4, wherein the first closed compartment is defined by the first and second vane assemblies, the exterior surface of the inner shaft and the interior surface of the delivery sheath.

8. The catheter system of claim 4, wherein the catheter system is configured to provide a deployment condition in which at least a portion of the each of the first and second vane assemblies is exposed distally beyond the distal end, and further wherein the deployment condition includes the wire management device defining first and second open compartments along the exposed portions of the first and second vane assemblies.

9. The catheter system of claim 8, wherein the deployment condition includes the exposed portion of the first and second vane assemblies bearing against native anatomy of a bodily vessel.

10. The catheter system of claim 8, wherein the catheter system is transitionable from the delivery condition to the deployment condition by at least one of proximally retracting the delivery sheath relative to the wire management device and distally advancing the wire management device relative to the delivery sheath.

11. The catheter system of claim 10, wherein the catheter system is configured such that transitioning of the catheter system from the delivery condition to the deployment condition includes the first closed compartment transitioning into the first open compartment, and the second closed compartment transitioning into the second open compartment.

12. The catheter system of claim 10, further comprising:
  a first guidewire slidably disposed within the first closed compartment; and
  a second guidewire slidably disposed within the second closed compartment.

13. The catheter system of claim 1, wherein the wire management device further includes a third vane assembly projecting from the exterior and defining a leading edge opposite the inner shaft, the third vane assembly being circumferentially spaced from the first and second vane assemblies relative to a circumference of the inner shaft, and further wherein the first-third vane assemblies and the delivery sheath combine to define first-third closed compartments.

14. The catheter system of claim 1, wherein the first and second vane assemblies each comprise a plurality of bristles.

15. The catheter system of claim 1, wherein the first and second vane assemblies are biased in a direction of a distal end of the wire management device.

16. The catheter system of claim 1, wherein the first and second vane assemblies each define a length, a height and a width, wherein the length is greater than the height, wherein the height is greater than the width in at least the expanded state, and further wherein the width in the collapsed state is substantially identical to the width in the expanded state.

17. The catheter system of claim 1, wherein the first and second vane assemblies each define a distal edge opposite a proximal edge, the distal and proximal edges each extending from the exterior surface of the inner shaft to the corresponding outer edge, and further wherein in the expanded state, projection of the distal edge from the exterior surface defines an acute angle.

18. The catheter system of claim 1, wherein the first and second vane assemblies are configured such that an exposed portion of the corresponding vane assembly initially located distal the distal end of the delivery sheath readily transitions from the expanded state to the collapsed state upon proximal retraction of the exposed portion into the lumen of the delivery sheath.

19. A wire management device for use with a delivery sheath to establish a plurality of compartments each sized to slidably receive a guidewire, the wire management device comprising:
  a shaft defining a centerline;
  a first vane assembly projecting from an exterior surface of the shaft and defining an outer edge opposite the shaft;
  a second vane assembly projecting from the exterior surface and defining an outer edge opposite the shaft, the second vane assembly being circumferentially spaced from the first vane assembly relative to a circumference of the shaft;
  wherein the first and second vane assemblies each comprise a plurality of bristles,
  wherein the first and second vane assemblies are collapsible to a collapsed state when disposed within a lumen of the delivery sheath, the collapsed state including the corresponding leading edge bearing against an interior surface of the delivery sheath;

and further wherein the first and second vane assemblies are configured to self-expand from the collapsed state toward a normal, expanded state when released from the lumen, a radial distance between the corresponding outer edge and the centerline in the expanded state being greater than the radial distance in the collapsed state.

20. A catheter system comprising:

a delivery sheath defining a lumen and a distal end;

a wire management device slidably disposed within the lumen, the wire management device including:

an inner shaft defining a centerline, a first vane assembly projecting from an exterior surface of the inner shaft and defining an outer edge opposite the inner shaft, a second vane assembly projecting from the exterior surface and defining an outer edge opposite the inner shaft, the second vane assembly being circumferentially spaced from the first vane assembly relative to a circumference of the inner shaft;

wherein the first and second vane assemblies are collapsible to a collapsed state when disposed within the lumen, the collapsed state including each of the first and second vane assemblies bearing against an interior surface of the delivery sheath;

and further wherein the first and second vane assemblies are configured to self-expand from the collapsed state toward a normal, expanded state when released from the lumen, a radial distance between the corresponding outer edge and the centerline in the expanded state being greater than the radial distance in the collapsed state;

and even further wherein the first and second vane assemblies each define a distal edge opposite a proximal edge, the distal and proximal edges each extending from the exterior surface of the inner shaft to the corresponding outer edge, and further wherein in the expanded state, projection of the distal edge from the exterior surface defines an acute angle relative to the centerline, wherein the distal edge of the first vane assembly extends from a trailing point at the exterior surface of the inner shaft to a leading point at the outer edge, and further wherein the leading point is distal the trailing point in the normal, expanded state.

* * * * *